United States Patent
Kelch (10) Patent No.: US 8,439,882 B2
(45) Date of Patent: May 14, 2013

(54) SYSTEM AND METHOD FOR USING MICRO-ELECTRO-MECHANICAL SYSTEMS (MEMS) TO HEAL WOUNDS

(75) Inventor: Randall P. Kelch, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 755 days.

(21) Appl. No.: 12/564,120

(22) Filed: Sep. 22, 2009

(65) Prior Publication Data

US 2010/0087791 A1    Apr. 8, 2010

Related U.S. Application Data

(60) Provisional application No. 61/102,662, filed on Oct. 3, 2008.

(51) Int. Cl.
*A61M 1/00* (2006.01)

(52) U.S. Cl.
USPC ......................................................... 604/313

(58) Field of Classification Search .................. 604/304, 604/313, 319, 361; 435/6.17, 7, 4, 335
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |

(Continued)

FOREIGN PATENT DOCUMENTS

| AU | 550575 A1 | 8/1982 |
|---|---|---|
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (and certified translation).

(Continued)

*Primary Examiner* — Melanie Hand (57) ABSTRACT

A system and method for treating a tissue site of a patient may include sensing one or more characteristics of exudate fluid of a tissue site of a patient. A level of the sensed one or more characteristics of the exudate fluid may be measured, and, in response to the measured at least one characteristic level, treatment may be applied or altered to the tissue site.

15 Claims, 5 Drawing Sheets

U.S. PATENT DOCUMENTS

| | | | |
|---|---|---|---|
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0173253 A1 | 8/2006 | Ganapathy et al. |
| 2008/0004549 A1 | 1/2008 | Anderson et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1 894 584 A2 | 3/2008 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO-03/063680 A2 | 8/2003 |
| WO | WO-2007/062024 A1 | 5/2007 |
| WO | WO-2008/040020 A2 | 4/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu, A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ž. ukić, Ð. Maksimović, Ð Radak, and P. Peška, "Vacuum Therapy in the Treatment of Peripheral Blood Vessels," *Timok Medical Journal* 11 (1986), pp. 161-164 (and certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (and certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, "*Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion date mailed Jan. 8, 2010; PCT International Application No. PCT/US2009/057757.

SYSTEM AND METHOD FOR USING MICRO-ELECTRO-MECHANICAL SYSTEMS (MEMS) TO HEAL WOUNDS

CROSS-REFERENCE TO RELATED APPLICATIONS

This application claims the benefit of U.S. Provisional Application No. 61/102,662, filed Oct. 3, 2008, which is incorporated herein by reference in its entirety.

BACKGROUND OF THE INVENTION

1. Field of the Invention

The principles of the present invention generally relate to a system and method for treating tissue. More specifically, the principles of the present invention relate to using micro-electro-mechanical systems (MEMS), also known as BioMEMS, with reduced pressure delivery systems to treat tissue.

2. Description of the Related Art

The field of wound therapy has advanced in recent years. One of the advancements of wound healing therapy has been the development of vacuum assisted wound healing or reduced pressure delivery to wounds. The application of reduced or negative pressure to a wound has been clinically shown to improve blood flow at the wound or tissue site, increase tissue growth, reduce infection, and improve healing time. Caregivers may use such vacuum assisted wound healing to treat a variety of chronic and acute wound types, such as pressure ulcers, diabetic wounds, abdominal wounds, partial-thickness burns, trauma wounds, flaps and grafts.

Background on Wounds and Wound Healing Processes

A wound is generally defined as a break in the epithelial integrity of the skin. Such an injury, however, may be much deeper, including the dermis, subcutaneous fat, fascia, muscle, and even bone. Proper wound healing is a highly complex, dynamic, and coordinated series of steps leading to tissue repair. Acute wound healing is a dynamic process involving both resident and migratory cell populations acting in a coordinated manner within the extra-cellular matrix environment to repair the injured tissues. Some wounds fail to heal in this manner (for a variety of reasons) and may be referred to as chronic wounds.

Following tissue injury, the coordinated healing of a wound will typically involve four overlapping but well-defined phases: hemostasis, inflammation, proliferation, and remodeling. Hemostasis involves the first steps in wound response and repair that are bleeding, coagulation, and platelet and complement activation. Inflammation peaks near the end of the first day. Cell proliferation occurs over the next 7-30 days and involves the time period over which wound area measurements may be of most benefit. During this time, fibroplasia, angiogenesis, re-epithelialization, and extra-cellular matrix synthesis occur. The initial collagen formation in a wound typically peaks in approximately 7 days. The wound re-epithelialization occurs in about 48 hours under optimal conditions, at which time the wound may be completely sealed. A healing wound may have 15% to 20% of full tensile strength at 3 weeks and 60% of full strength at 4 months. After the first month, a degradation and remodeling stage begins, wherein cellularity and vascularity decrease and tensile strength increases. Formation of a mature scar often requires 6 to 12 months.

Efforts in the Related Art to Measure Wound Healing Processes

Because wound treatment can be costly for both materials and professional care time, assessment of the wound and the wound healing process can be essential. There are a few wound parameters that may assist a caregiver in determining healing progress of a wound. For example, wound area and volume measurements may provide a caregiver with knowledge as to whether or not a wound is healing and, if the wound is healing, how rapidly the wound is healing.

In addition to size and volume of a wound, caregivers often use color and texture of a wound in determining wound health and healing progress. Wound tissue includes a wound bed and periwound areas or wound edges. Certain problems may be detected from the color and texture of wound tissue. For example, normal granulation tissue has a beefy, red, shiny textured appearance and bleeds readily, whereas necrotic tissue (i.e., dead tissue) may either be yellow-gray and soft, generally known as "slough" tissue, or hard and black/brown in color, generally known as "eschar" tissue. A caregiver may observe and monitor these and other wound tissues to determine wound healing progress of the overall wound and specific wound regions. Wound assessment is an important process to properly treat a wound, as an improper or incomplete assessment may result in a wide variety of complications. Infections at a tissue site that go untreated may result in permanent damage, amputation, or even death to a patient.

Infections can start slowly, but increase rapidly. If an infection increases too rapidly, a patient can become seriously ill over a short span of time. During treatment of a wound, bandages or other dressing typically cover the wound. As such, caregivers cannot see the wound except when the dressing is removed or changed. Depending on the size and type of wound, the dressing may be changed less regularly to avoid disrupting the healing process of the wound. During the intervals of changing the wound, an infection may form without a caregiver knowing that an infection has started or how quickly the infection is progressing. Other problems may develop during the wound healing process while the wound is covered by the dressing, and may go unnoticed until the dressing is changed.

SUMMARY OF THE INVENTION

To provide a caregiver with an improvement in being able to assess healing and infection status of a tissue site of a patient, the principles of the present provide for measurement of one or more characteristic of exudate fluid from a tissue site. The exudate fluid may be measured for chemical characteristic (e.g., pH level), biological marker (e.g., bacteria count or type), or any other indicator of chemical characteristic(s) and/or biological marker(s) to assist a caregiver in treating a tissue site. One embodiment for measuring one or more characteristic of exudate fluid includes using a micro-electro-mechanical system (MEMS) placed at or near the tissue site. By integrating the MEMS device into a reduced pressure delivery system that is operating to treat the tissue site using reduced pressure, the reduced pressure delivery system may adjust one or more treatment parameters to compensate for undesired characteristics of exudate fluid from a tissue site in response to a MEMS device sensing one or more characteristics of the exudate fluid.

One embodiment of a reduced pressure delivery system may include electromechanical components configured to apply treatment to a tissue site of a patient. A processing unit may be in communication with the electromechanical components and be configured to cause the electromechanical components to activate to apply the treatment to the tissue site. At least one conduit may be configured to deliver the treatment to the tissue site. A micro-electro-mechanical (MEMS) device configured to sense one or more characteristic of exudate fluid from the tissue site, and further be configured to communicate data indicative of the sensed exudate fluid characteristic(s). The processing unit may be configured to receive the data from said MEMS device and cause the electromechanical components to apply the treatment to the tissue site of the patient via the conduit(s).

One embodiment of a method for treating a tissue site of a patient may include sensing one or more characteristic of exudate fluid of a tissue site of a patient. A level of the sensed characteristic(s) of the exudate fluid may be measured, and, in response to the measured characteristic(s) level, treatment may be caused to be applied or altered to the tissue site.

DETAILED DESCRIPTION OF THE DRAWINGS

Figure 1:
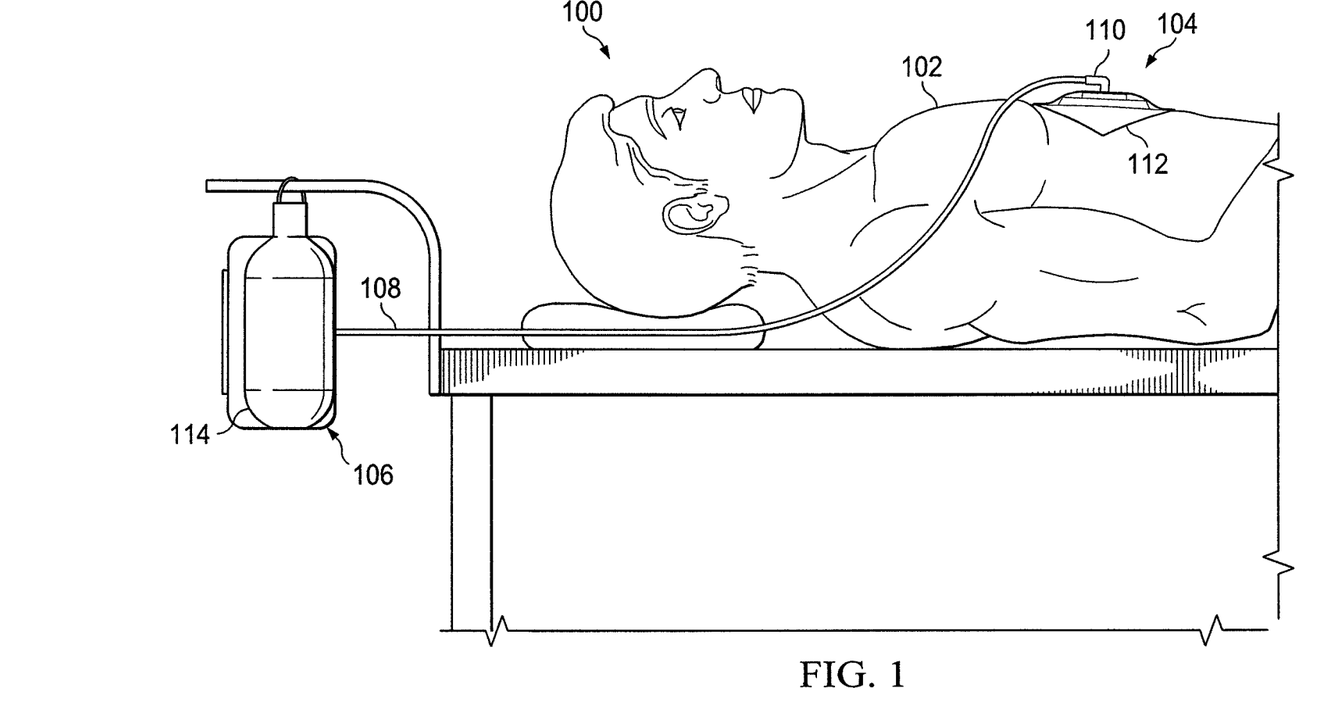
FIG. 1 is an illustration of an exemplary configuration of a patient being treated using a reduced pressure delivery system.

With regard to FIG. 1, a setup 100 for treating a patient 102 is shown. The patient is receiving reduced pressure treatment at a tissue site 104 by a reduced pressure delivery system 106. The reduced pressure delivery system 106 is also known as a vacuum assisted therapy device. The reduced pressure delivery system 106 may be any system that is generally utilized to assist a patient in the process of tissue treatment, such as wound healing. Still yet, the reduced pressure delivery system 106 may be any computing system that is configured to utilize software as described further herein to assist a caregiver with monitoring healing of the tissue site 104. A caregiver generally means any medical professional, user, family member of a patient, or patient who interacts or interfaces with a reduced pressure delivery system. In an alternative embodiment, the reduced pressure delivery system may be integrated into an integrated dressing that may be utilized for treating a mobile patient.

The term "tissue site" as used herein refers to a wound or defect located on or within any tissue, including but not limited to, bone tissue, adipose tissue, muscle tissue, neuro tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The term "reduced pressure" as used herein generally refers to a pressure less than the ambient pressure at a tissue site that is being subjected to treatment. In most cases, this reduced pressure will be less than the atmosphere pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual vacuum level applied to the tissue site may be significantly less than the vacuum level normally associated with a complete vacuum. Reduced pressure may initially generate fluid flow in the tube or conduit in the area of the tissue site. As the hydrostatic pressure around the tissue site approaches the desired reduced pressure, the flow may subside, and the reduced pressure is then maintained. Unless otherwise indicated, values of pressures stated herein are gage pressures.

The reduced pressure delivery system 106 may include a reduced pressure conduit 108 that extends from the reduced pressure delivery system 106 to the tissue site 104. At the tissue site 104, a reduced pressure dressing 110 that may include a distribution manifold (not specifically referenced) that may be fluidly connected to the reduced pressure conduit 108. In addition, a drape 112 may be placed over the tissue site 104 and distribution manifold 110. The term "manifold" as used herein generally refers to a substance or structure that is provided to assist in applying reduced pressure to, delivering fluids to, or removing fluids from a tissue site. A manifold typically includes a plurality of flow channels or pathways that interconnect to improve distribution of fluids and pressure provided to and removed from the area of tissue around the manifold. Examples of manifolds may include, without limitation, devices that have structural elements arranged to form flow channels, cellular foams, such as open cell foam, porous tissue collections, and liquids, gels and foams that include or cure to include flow channels.

The drape 112 may be a flexible material that is gas permeable and prevents liquids from entering or exiting the tissue site 104 during reduced pressure treatment. The flexible material is an object or material that is able to be bent or flexed. Elastomer materials are typically flexible, but reference to flexible materials herein does not necessarily limit material selection to only elastomers. The use of the term "flexible" in connection with a material or reduced pressure delivery apparatus in accordance with the principles of the present invention generally refers to the material's ability to conform to or closely match the shape of a tissue site. For example, the flexible nature of a reduced pressure delivery apparatus used to treat a bone defect may allow the apparatus to be wrapped or folded around the portion of the bone having the defect.

The reduced pressure delivery system 106 may include an exudate canister 114 that collects exudate fluid. As shown, the exudate canister 114 is shown to protrude from the reduced pressure delivery system 106 so that a user may view a level of exudate fluid if the exudate canister 114 is at least partially translucent. Alternatively, the exudate canister 114 may be in fluid communication with the reduced pressure delivery system 106 through an intermediate tube (not shown), for example.

In one embodiment, a MEMS device (not shown) may be integrated into the reduced pressure conduit 108, reduced pressure dressing 110, exudate canister 114 at the reduced pressure delivery system 106, applied directly to the tissue site 104, or otherwise positioned within a fluid path of the reduced pressure delivery system 106. A MEMS device is generally considered an integration of mechanical elements, sensors, actuators, and electronics, or combination thereof, on a common substrate using micro-fabrication technology, and can perform for one or more functions through use of the integration of the mechanical and electrical components. The functions for the reduced pressure delivery system 106 may include sampling and sensing, generating feedback signals, and delivering or causing treatment to be delivered to the tissue site 104. Such a feedback is generally considered an active feedback in an automatic control system. The "fluid path" is a path that exudate fluid travels from and including the tissue site 104 to and including the exudate canister 114. The MEMS device may be fixedly attached or removably positioned in the fluid path to sample the exudate fluid from the tissue site 104. While many parameters may be measured in the fluid path away from the tissue site, certain parameters, such as temperature and pressure, are more accurately measured at the tissue site. The term "fluid" as used herein generally refers to a gas or liquid, but may also include any other flowable material, including but not limited to gels, colloids, and foams. One example of a gas is air.

Figure 2:
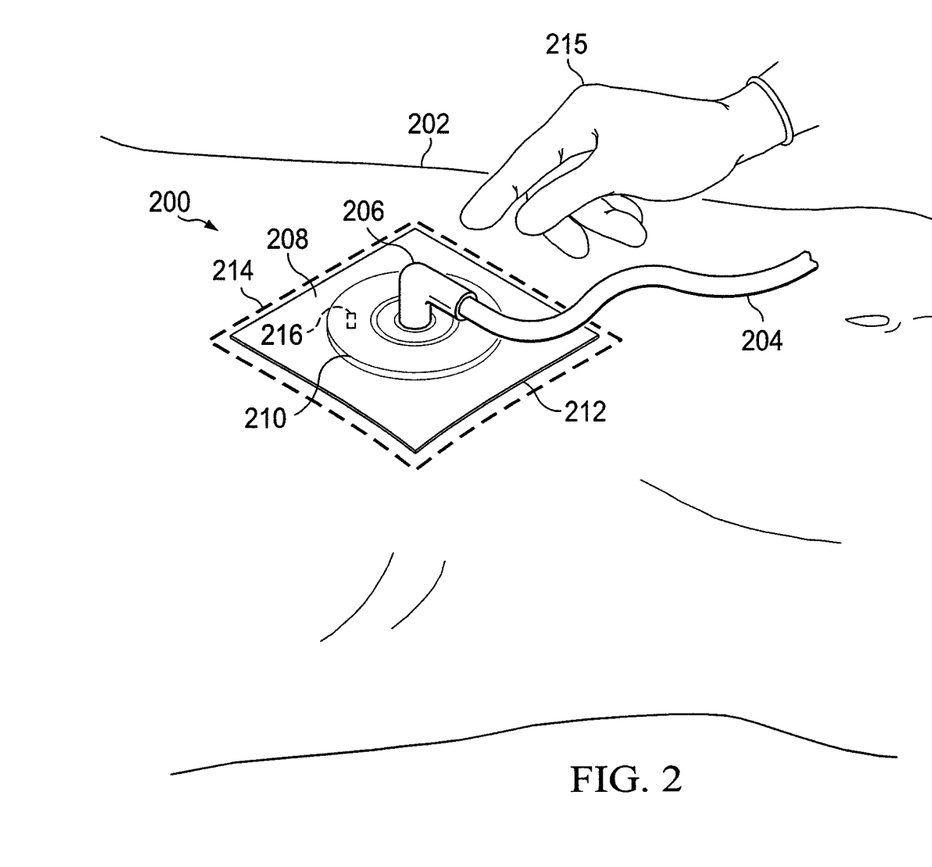
FIG. 2 is an illustration of an exemplary dressing covering a tissue site to which reduced pressure is being applied by a reduced pressure delivery system, a MEMS device being included within a fluid path of the tissue site to a reduced pressure delivery system.

With regard to FIG. 2, a tissue site 200 on a person's body 202 is receiving reduced pressure therapy from a reduced pressure delivery system (not shown). It should be understood that the reduced pressure delivery system may be similarly utilized on an animal's body. The reduced pressure delivery system is connected to a reduced pressure conduit 204 and in fluid communication with a distribution manifold 210, either directly or via an adapter 206. A drape 208 may be configured to cover the distribution manifold 210, which is shown to be pressing into the drape 208. The drape 208 covers tissue at the tissue site 200, thereby helping to maintain a seal formed at an intersection 212 of the drape 208 and surrounding tissue 214 at the tissue site 200 so that fluids, such as air, cannot enter or exit the tissue site 200. A caregiver may use his or her hand 215 to press the drape 208 onto healthy tissue on the person's body 202 surrounding the tissue site 200 to form a seal. By preventing fluids from entering or exiting the tissue site 200, the tissue site 200 may receive maximum benefit of the reduced pressure therapy, including minimizing chance for additional infection, improving growth of tissue, reducing edema, etc.

A MEMS device 216 may be positioned within the fluid path between the tissue site 200 and reduce pressure delivery system. The MEMS 216 device may be affixed to the manifold, reduced pressure conduit 204, drape 208, or anywhere else within the fluid path. In one embodiment, the MEMS device 216 is configured to communicate wirelessly with the reduced pressure delivery system. A wireless MEMS device is sometimes referred to as a wireless integrated micro-system (WIMS). Alternatively, the MEMS device 216 may be configured to have a wired connection to the reduced pressure delivery system. If wireless, the MEMS device 216 may be configured to use any wireless communication protocol to communicate with the reduced pressure delivery system. For example, Bluetooth® wireless communication protocol may be utilized since the reduced pressure delivery system is generally within range to form a Bluetooth® communication path.

The MEMS device 216 may be configured to sample exudate fluid from the tissue site 200. In one embodiment, the MEMS device 216 may be configured to determine one or more specific characteristics of the exudate fluid, such as pH level or $O_2$ level, which may help determine tissue oxygenation. For the purposes of this description, a characteristic of exudate fluid refers to chemical composition, chemical characteristic, biological marker, or any other characteristic of exudate fluid that is measurable by the MEMS device 216. Alternatively, the MEMS device 216 may be configured to sample and collect raw data of the exudate fluid. The MEMS device 216 may communicate either the raw data or processed data to the reduced pressure delivery system.

Still yet, the MEMS device 216 may be configured to sense humidity at the tissue site. Humidity at a wound site that is too low may cause dessication of the wound. By sensing humidity, the reduced pressure delivery system may ensure that would dessication does not occur. In one embodiment, a predetermined minimum threshold level may be established to trigger an alarm or alter operation of the reduced pressure delivery system by initiating fluid delivery to the tissue site. For example, a minimum threshold level of 95% humidity may be set such that when the humidity drops below 95%, the reduced pressure delivery, system delivers a treatment fluid to the tissue site. A second minimum threshold level of 90% may be set such that in response to the humidity dropping below the second minimum threshold level, an alarm may be generated to notify a caregiver of the situation. In an alternative embodiment, moistness of the tissue site itself may be sensed by the MEMS device 216.

Figure 3:
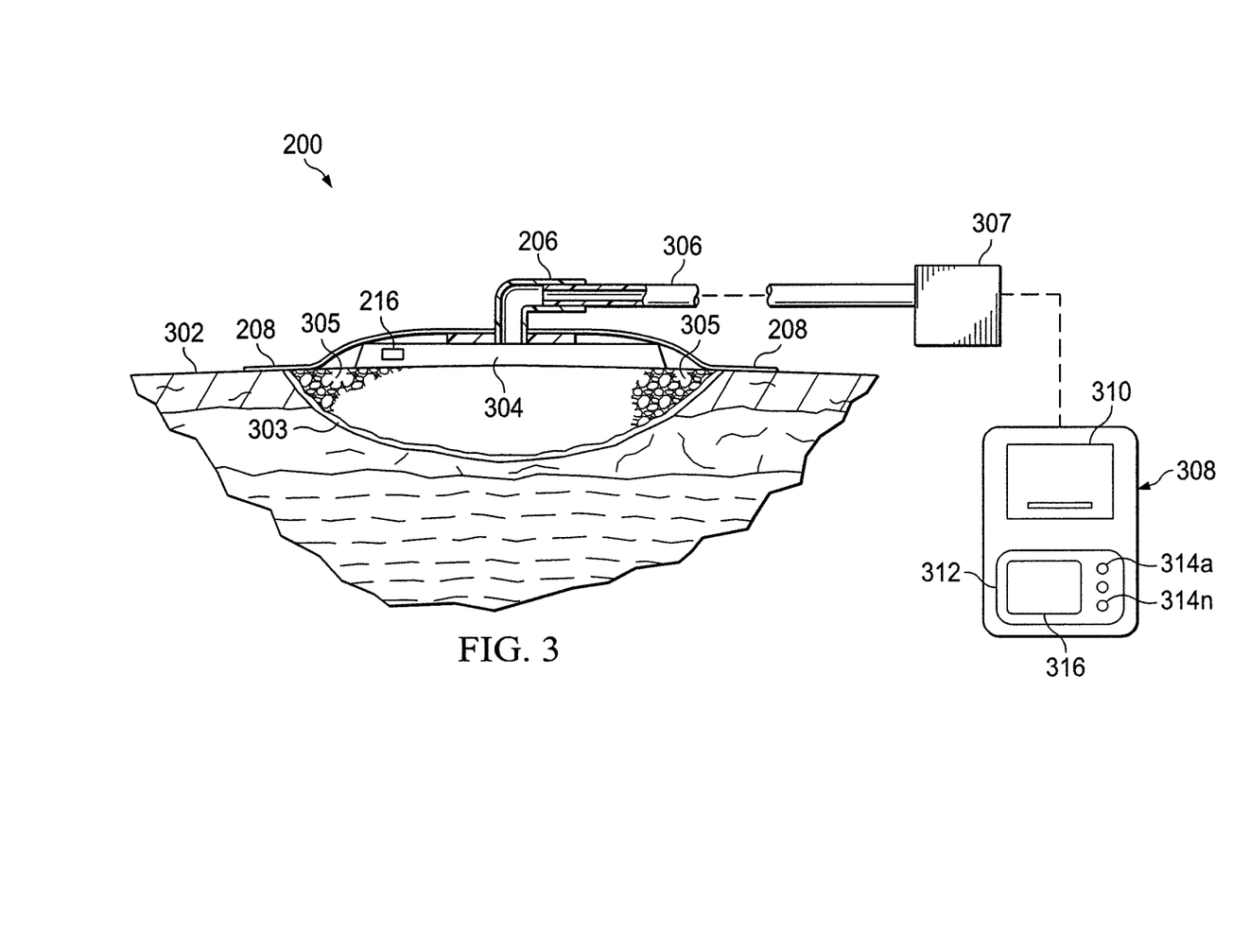
FIG. 3 is an illustration of an exemplary dressing covering a tissue site, a MEMS device being included within a fluid path of the tissue site to a reduced pressure delivery system.

With regard to FIG. 3, a cutout view of the tissue site 200 is provided to show the drape 208 extending over healthy tissue 302 surrounding tissue 303, such as wound tissue, at the tissue site 200. The drape 208 extends over manifold 304 and dressing foam 305, which is in fluid communication with reduced pressure conduit 306. The drape 208, manifold 304, and dressing foam 305 are all part of the dressing, as understood in the art. It should be understood that the dressing may be formed of additional, fewer, and/or different components, as understood in the art. The reduced pressure conduit 306 is further in fluid communication with reduced pressure delivery system 308. Valves 307, which may be internal or external of the reduced pressure delivery system 308, may be controllable by the reduced pressure therapy system 308 to enable reduced pressure and/or treatment fluid to be applied or altered to the tissue site 200. The reduced pressure therapy system 308 may include a vacuum pump 310 and electronic display 312. The electronic display 312 may include control elements 314a-314n (collectively 314) that may be used by a user operating the reduced pressure delivery system 308. In addition or alternatively, the electronic display 312 may include a touch-screen electronic display 316 that enables the user to interface with and operate the reduced pressure delivery system 308. A more detailed illustrative reduced pressure delivery system is provided in FIG. 4A.

The MEMS device 216 is shown to be beneath the drape 208 and attached to or otherwise in contact with the manifold 304. By positioning the MEMS device 216 as close to the tissue 303 at the tissue site 200 as possible, the MEMS device 216 can collect and/or produce as accurate a reading of the characteristic(s) (e.g., chemical characteristic and/or biological marker) of the exudate fluid as possible. In one embodiment, the MEMS device 216 may be placed in contact with the tissue site 200 to measure certain parameters that are more accurately measured when the MEMS device 216 is in contact with the tissue site 200.

The reduced pressure delivery system 308 may receive data via one or more signals communicated from the MEMS device 216. The data may include raw data or processed data indicative of the characteristic(s) of the exudate fluid. As understood in the art, the MEMS device 216 may be configured to sample any type of characteristic, including a chemical characteristic and/or biological marker. For example, the MEMS device 216 may be configured to sample and measure pH level of the exudate fluid, bacteria count or type in the exudate fluid, or any other chemical characteristic and/or biological marker in the exudate fluid that can help assist a caregiver in treating the patient. The MEMS device 216 may additionally or alternatively be configured to sense environmental factors, such as pressure, temperature, and humidity, as previously described. An illustrative MEMS device that may be used or modified, and used for sensing pressure to wirelessly communicate pressure readings to the reduced pressure delivery system 308 is produced by Integrated Sensing Systems (ISSYS) located in Ypsilanti, Mich. USA. Other MEMS sensors produced by ISSYS or other manufactures for sensing other chemical characteristic, biological marker, and/or environmental conditions may be utilized in accordance with the principles of the present invention.

Figure 4A:
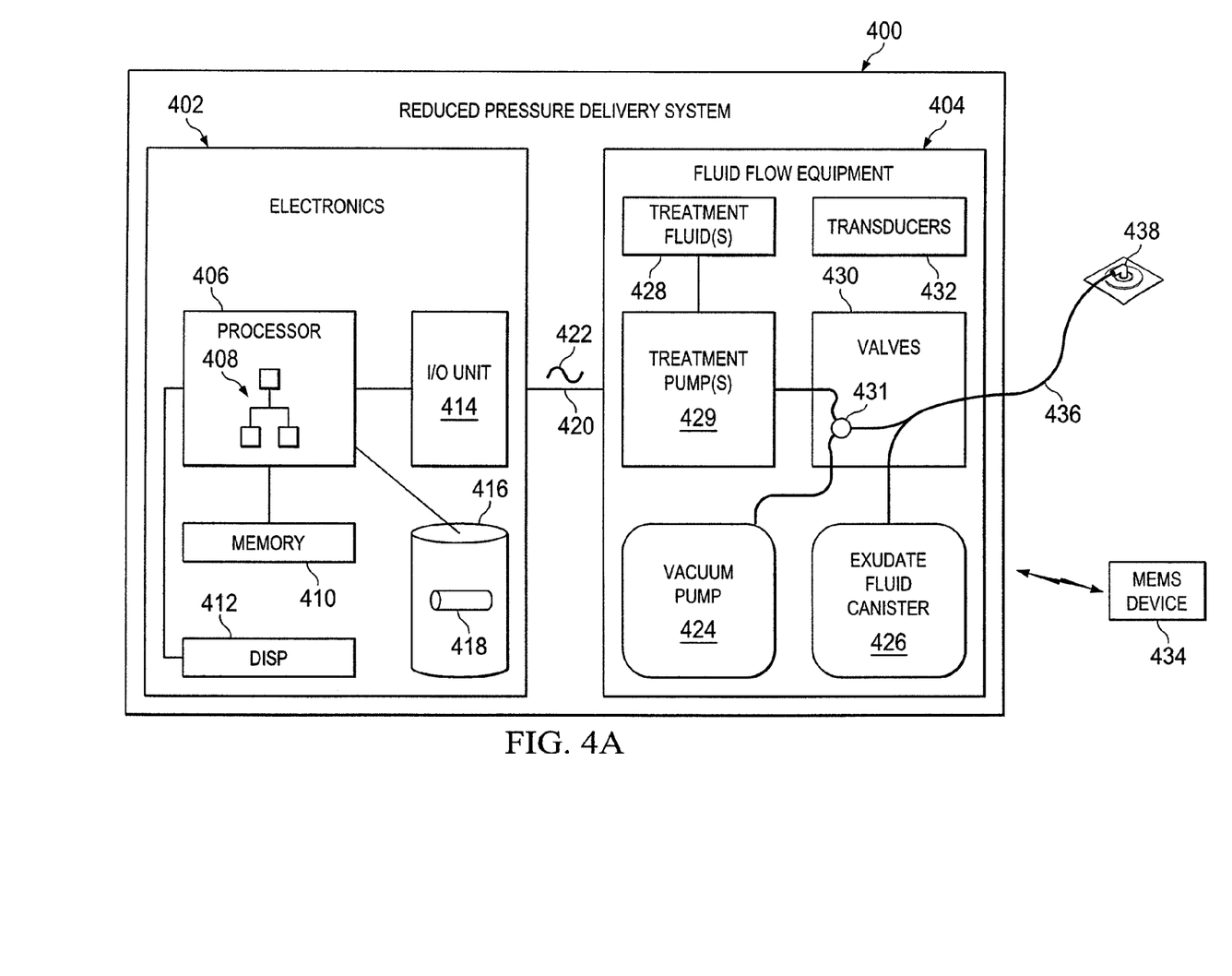
FIG. 4A is a block diagram of an exemplary reduced pressure delivery system.

With regard to FIG. 4A, an exemplary reduced pressure delivery system 400 is shown to be configured with electronics 402 and fluid flow equipment 404. The electronics may include a processing unit 406 that executes software 408. The software 408 may be configured to control and manage operation of the reduced pressure delivery system 400. The processing unit 406 may be in communication with a memory 410, display 412, input/output (I/O) unit 414, and storage unit 416. The storage unit may store a data repository 418, which may be a database, for storing setting information or information associated with one or more patient on whom treatment is applied by the reduced pressure delivery system 400. It should be understood that the data repository 418 may be configured of one or more data files, as understood in the art. The memory 410 may be used by the processing unit 406 for storing operation information, such as settings and operational status of one or more features of the reduced pressure delivery system 400. The display 412 may be an electronic display that provides a user interface, such as a graphical user interface, and may be touch sensitive to enable a caregiver to control the reduced pressure delivery system. The I/O unit 414 may be configured to communicate locally (i.e., at the reduced pressure delivery system 400) or remotely (e.g., with devices over a network or with a remotely located MEMS device).

The electronics 402 may communicate with the fluid flow equipment 404 for controlling operation of electromechanical components. The electromechanical components may include a vacuum pump 424, exudate fluid canister 426, and treatment fluid(s) 428. Other electromechanical components may include transducers, such as flow, tissue pressure, and pump pressure transducers, as understood in the art. Filters (not shown) may also be included in the fluid flow equipment 404. The vacuum pump 424 may be configured to create a reduced pressure that is used to apply a reduced pressure at a tissue site of a patient. The exudate fluid canister 426 may be a container, such as a plastic container, that is integrated into or separate from the reduced pressure delivery system 400 and used to collect exudate fluid from a patient being treated by the reduced pressure delivery system 400.

The treatment fluid(s) 428 may include one or more treatment fluids that are used for treating a patient. For example, the treatment fluid(s) 428 may include anti-bacterial or antiseptic fluids that help reduce bacteria at a tissue site. As another example, the treatment fluid(s) 428 may include one or more pH balance fluid (e.g., acidic or basic fluids) that may be applied or altered to the tissue site to adjust pH balance. Still yet, the treatment fluid(s) 428 may include a saline or other cleanser fluid that may be used to clean, irrigate, or humidify the tissue site. In general, any biological marker or medicinal fluids may be utilized as treatment fluids in accordance with the principles of the present invention.

One or more treatment pumps 429 may be configured to pump the treatment fluid(s) 428 to the tissue site. The treatment pump(s) 429 may be any pump that is capable of pumping fluid, such as pneumatic and electromechanical pumps.

The processing unit 406, which may include one or more processors, may be configured to communicate with fluid flow equipment, including valves 430 and transducers 432 for controlling operation of the reduced pressure delivery system 400. The software 408 may control the processing unit 406 to turn on/off the vacuum pump 424 and open/close valves 430, including an actuating device 431, such as a valve, in response to receiving information from transducers 434 or other sensors.

A MEMS device 434, which may also be considered a WIMS device as wireless communications are performed by the MEMS device 434, may be positioned within a fluid path at or between a tissue site of a patient and exudate fluid canister 426 at the reduced pressure delivery system 400. The MEMS device 434 may be configured to (i) sample or (ii) sample and measure characteristic(s) of the exudate fluid. The MEMS device 434 may be configured to be wired or wireless to communicate a data signal with the reduced pressure delivery system 400. In communicating either wired or wirelessly, the MEMS device 434 may communicate using either analog or digital communications techniques and any communications protocol as understood in the art. The data signal may include raw or processed data representative of characteristic data (e.g., pH level) of the exudate fluid.

The MEMS device 434 may be configured to sample the exudate fluid to measure one or more chemical characteristic for O2 level, CO2 level, chemical markers, and other chemical characteristic. Additionally and/or alternatively, the MEMS device 434 may be configured to sample the exudate fluid to measure biological marker for microorganisms, biomarkers, proteins (e.g., albumin), and other biological markers. Still yet, the MEMS device 434 may be configured to measure temperature of the exudate fluid, which may be indicative of an infection or other process occurring at the tissue site. In one embodiment, rather than using transducers 432 for controlling reduced pressure operation, the MEMS device 434 may be used by the reduced pressure delivery system 400 for controlling reduced pressure operation.

In one embodiment, the reduced pressure delivery system 400 may be configured to deliver treatment fluids, such as cleanser fluids or medicinal fluids, to the tissue site for cleansing or treating. To clean or treat the tissue site, in response to the MEMS device 434 sensing one or more chemical characteristic and/or biological marker of exudate fluid, the processing unit 406 may display information representative of the sensed characteristic(s) of the exudate fluid on an electronic display (e.g., bar graph) or create an audio output (e.g., tone or voice output). Alternatively and/or additionally, the processing unit 406 may cause the treatment fluid(s) to be applied or altered to the tissue site via one or more conduits 436 connected to a dressing 438. In one embodiment, each treatment fluid may be delivered to the tissue site using the same or different conduit as other treatment fluids. If multiple conduits are used to deliver the treatment fluid(s) 428, then multiple valves or actuating devices may be used to control delivery of the respective treatment fluid(s) 428. The treatment fluid(s) may be delivered via the same or different conduits as used for delivering reduced pressure to the tissue site.

In one embodiment, the conduit(s) 436 include a reduced pressure conduit for applying reduced pressure to the tissue site and separate conduits, for applying the treatment fluid(s) 428. Alternatively, the same conduit may be utilized for both applying the reduced pressure and treatment fluid(s) 428, but in such a configuration, the treatment pump(s) 429 and vacuum pump 424 are to be operated at different times or the valves 430 are to limit fluid communication of the treatment pump(s) 429 and vacuum pump 424 to the conduit(s) 436. The processing unit may be in electrical communication with the actuating device 431 and set the actuating device 431 in a configuration to cause the vacuum pump 424 to apply or alter reduced pressure to the tissue site in a first state and communicate a delivery signal 422 via communication line 420 from the electronics 402 to the fluid flow equipment 404 to configure the actuating device 431 in a second state to apply treatment fluid(s) 428 to the tissue site. In determining whether to configure the actuating device 431 in the first or second state, a predetermined therapy may be followed by the processor 406, where the predetermined therapy may respond to one or more characteristics of the exudate fluid sensed by the MEMS device 434. Furthermore, depending on the treatment fluid that is being delivered, the processing unit 406 may be configured to stop the vacuum pump 424 for a certain period of time to allow the tissue site to be treated with medicine, for example, or operate the vacuum pump 424 while cleansing the tissue site, for example. It should be understood that a variety of treatment operations may be utilized to deliver the treatment fluid 428 and control the vacuum pump 424 in response to the MEMS device 434 sampling characteristic(s) of exudate fluid from the tissue site. For example, the processing unit 406 may be configured to alter the reduced pressure treatment in response to determining that the exudate fluid is increasing in acidity. Still yet, the processing unit 406 may be configured to create a notification or alarm, visual or audible, to notify a caregiver of a high or low level of a chemical characteristic and/or biological marker in the exudate fluid. In one embodiment, the processing unit 406 may be configured to display a graphical (e.g., graph, pie chart, or bar) or alphanumerical display (e.g., number or grade) to represent a level of chemical characteristic and/or biological marker in the exudate fluid. The processing unit 406 may further be configured to generate and display a graphical or alphanumerical display of environmental conditions, such as temperature, pressure, and humidity that are sensed by the MEMS device. It should be understood that one or more MEMS devices may be utilized to perform one or more sensing and/or measuring functions.

Figure 4B:
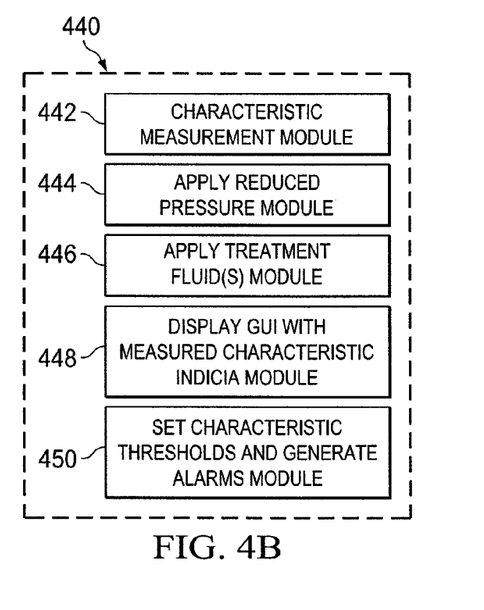
FIG. 4B is a block diagram of exemplary modules configured to control operation of the reduced pressure delivery system of FIG. 4A.

With regard to FIG. 4B, modules 440 may be configured to control operation of the reduce pressure delivery system 400 (FIG. 4A). The modules 440 may be software, such as software 408 executed by processing unit 406, hardware, or combination thereof. The modules 440 may include a characteristic measurement module 442, apply reduced pressure 444, apply treatment fluid(s) module 446, display GUI with measured characteristic indicia module 448, and set characteristic thresholds and generate alarms module 450. The modules 440 are exemplary and may be divided, combined, or configured in some other manner. Furthermore, additional and/or different modules may be utilized to perform the same or similar functionality in accordance with the principles of the present invention.

The characteristic measurement module 442 may be configured to measure one or more characteristic of exudate fluid sensed by a MEMS device. In one embodiment, the MEMS device may communicate raw data to the characteristic measurement module 442 to compute levels of whatever characteristic is being sensed. In an alternative embodiment, the characteristic measurement module 442 is configured within the MEMS device itself and reports a computed characteristic level or value to the reduced pressure delivery system 400. Multiple MEMS devices may be used to sense and process characteristics of exudate fluid.

The apply reduced pressure module 444 may be configured to control electromechanical equipment in the reduced pressure delivery system 400 to apply reduced pressure to a tissue site of a patient. The reduced pressure module 444 may be configured to apply a constant reduced pressure or intervals of reduced pressure. In one embodiment, the reduced pressure module 444 may utilize one or more levels determined by the characteristic measurement module 442 to determine an amount of reduced pressure to apply to the tissue site, including whether the reduced pressure being applied to the tissue site should be stopped. For example, if a level of bacteria is determined to be high, then the reduced pressure may be temporarily halted by the reduced pressure module 444 until treatment fluid may be applied or altered to the tissue site, and then the reduced pressure module 444 may re-apply reduced pressure to the tissue site.

The apply treatment fluid(s) module 446 may be configured to control electromechanical components within the reduced pressure delivery system 400 to apply treatment fluids to the tissue site of a patient. The electromechanical components may include a pump, valves, and any other electromechanical components used to control treatment fluid to be applied or altered to the tissue site. In addition, the apply treatment fluid(s) module 446 may be configured to control concentration of treatment fluids being applied or altered to the tissue site by controlling the electromechanical components to adjust mixture of fluids or other materials (e.g., powder) to form a treatment fluid. In operation, the apply treatment fluid(s) module 446 may be configured (i) to receive a characteristic level in the exudate fluid, (ii) to determine amount, concentration, and/or duration of treatment fluid to apply to a tissue site of a patient, and (iii) to apply treatment fluid(s) to the tissue site by controlling the electromechanical components in the reduced pressure delivery system 400.

The display GUI with measured characteristic indicia module 448 may be configured to receive a characteristic level in the exudate fluid and display a graphical and/or alphanumeric representation of the characteristic level on an electronic display. The GUI may display any graphical representation that indicates to a caregiver the level of the characteristic. For example, a pH level may be shown on a bar graph, numerically, pie graph, or any other format that a caregiver can view the pH level of the exudate fluid.

The set characteristic thresholds and generate alarms module 450 may be configured with pre-established thresholds, maximum and minimum, or enable a caregiver to establish or set thresholds of levels for characteristics of exudate fluid. The alarms may be visual and/or audible. In setting the thresholds, the module 450 may provide a menu with pre-established thresholds and enable a caregiver to alter the thresholds on a case-by-case basis. For example, a caregiver may set thresholds for maximum and minimum levels for pH levels at 6.5 and 7.5, respectively. As another example, a maximum threshold may be set for bacteria count at 75. If the reduced pressure delivery system 400 is configured to automatically apply treatment fluids to a tissue site, then an alarm indicating that the characteristic level crosses a threshold may indicate to the caregiver that the reduced pressure delivery system 400 is having difficulty altering or maintaining the characteristic. If not automated, the alarm may signal a caregiver that the tissue site or patient is having a problem.

Figure 5:
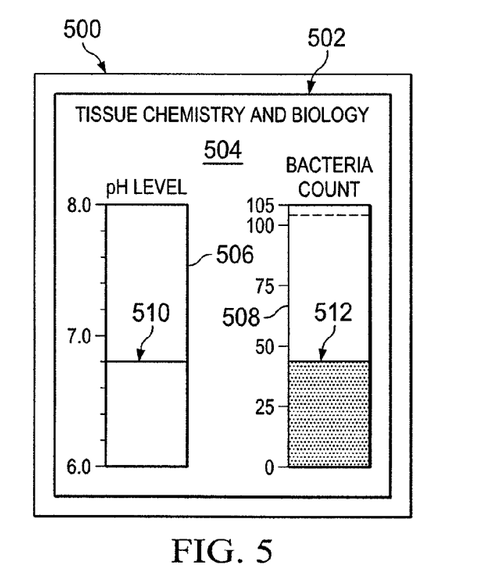
FIG. 5 is an illustration of an exemplary reduced pressure delivery system that includes an electronic display for displaying an exemplary graphical user interface.

With regard to FIG. 5, an exemplary reduced pressure delivery system 500 that includes an electronic display 502 displaying an exemplary graphical user interface (GUI) 504 is shown. The GUI 504 may be configured to display one or more indicators of chemical characteristics and biological marker being sensed by one or more MEMS devices. As shown, two bar indicators 506 and 508 are being used to display levels of pH balance and bacteria count, respectively. The bar indicator 506 may display an indicia 510 in the form of an arrow with a line extending across the bar indicator 506 to represent a measured pH level. In one embodiment, the indicia 510 may change color depending on the value of the pH level of exudate fluid sensed by the MEMS device. In another embodiment, an alphanumeric indicia, such as a number, may be displayed in place of or in addition to the bar indicator 506. Still yet, historical values of the pH level may be displayed (e.g., measurement of pH level every hour) or displayable via a request.

The bar indicator 508 may be configured to display bacteria count of exudate fluid by the MEMS device. The bar indicator 508 may display a level in the form of a dynamic indicia 512 that increases and decreases in response to a MEMS device sensing bacteria and determining a bacteria count. The bacterial count may be performed over a period of time if bacteria samples are to be cultured by the MEMS device, so the dynamic indicia 512 may be a delayed indicator (e.g., indicator from an exudate fluid sample from 12 hours earlier) as to the bacteria count. The dynamic indicia 512 may change color depending on the bacteria count. For example, if the bacteria count is below a certain level (e.g., 25), then the dynamic indicia 512 may be displayed in green to enable a caregiver to readily determine that bacteria count is in check. If the bacteria count exceeds a different level (e.g., 75), then the dynamic indicia 512 may be displayed in red to alert the caregiver that bacteria levels are too high and appropriate action is to be taken. In one embodiment, one or more alarms in the form of audible and/or visual indicators may be utilized to notify a caregiver that either the pH level or bacteria count has increased over a predetermined level. It should be understood that the bar indicators 506 and 508 are exemplary and that any other type of graphical or alphanumeric indicator may be utilized to provide a caregiver with information of characteristics of exudate fluid that is being sensed by one or more MEMS devices.

In addition to the reduced pressure delivery system 500 being capable of displaying graphical indicators for a caregiver to monitor chemical characteristic(s) and/or biological marker status of a tissue site being treated, the principles of the present invention may further provide for the reduced pressure delivery system 500 to deliver treatment fluids to the tissue site automatically based on the sensed characteristic(s) of the exudate fluid. For example, if the pH level increases above 7.0, then an acidic treatment fluid may be delivered to the tissue site by the reduced pressure delivery system 500. Depending on the pH level, the acidic treatment fluid may be delivered for a different duration of time. For example, for a pH level of 7.5, an acidic treatment fluid may be delivered for two minutes, and for a pH level of 8.5, an acidic treatment fluid may be delivered for eight minutes. Alternatively, the treatment fluid may be set at a different level of pH (i.e., have a different concentration of acidity or alkalinity), so that the treatment fluid may be delivered for the same duration of time even if measured pH levels are different. In one embodiment, the pH level of the treatment fluid may be automatically altered by adjusting concentration of acid in the treatment fluid.

If it is determined by the reduced pressure delivery system 500 that the bacteria count has increased above a certain level, an antiseptic treatment fluid may be delivered to the tissue site. In one embodiment, the antiseptic treatment fluid may be adjusted to address the bacteria count. For example, if the bacteria count is relatively low, then a relatively low concentration of antiseptic treatment fluid may be delivered to the tissue site. As the bacteria count increases, so too may the antiseptic treatment fluid increase. The concentration of the antiseptic may be altered by increasing and decreasing an aperture or valve to add or reduce antiseptic fluid with another fluid, such as a cleanser fluid (e.g., saline solution), to create an antiseptic treatment fluid for delivery via a conduit to the tissue site. After delivery of the antiseptic treatment fluid, a cleanser fluid may be used to rinse the tissue site. It should be understood that reduced pressure may be paused while the tissue site is being treated with the treatment fluid and, once treatment is complete, the reduced pressure may be resumed to initiate reduced pressure treatment and remove the treatment fluid and exudate fluid from the tissue site.

Figure 6:
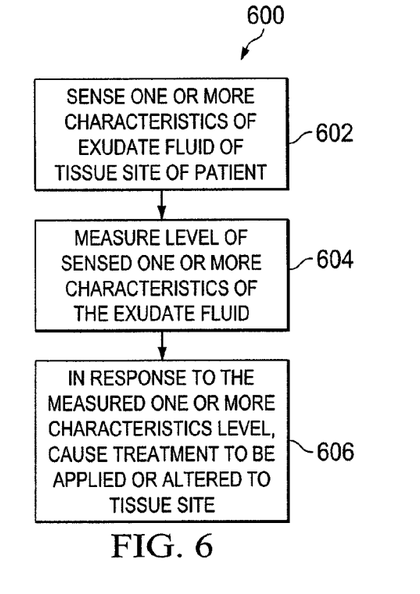
FIG. 6 is a flow diagram of an exemplary process for sensing one or more characteristic of exudate fluid at a tissue site of a patient and delivering treatment fluid to the tissue site in response thereto.

With regard to FIG. 6, an exemplary flow chart 600 is shown. The process starts at step 602, where characteristic(s) of exudate fluid of a tissue site of a patient may be sensed. The characteristic(s) of exudate fluid may be sensed by a MEMS device, which may sample the exudate fluid and communicate raw data or processed data to a reduced pressure delivery system. The MEMS device may be configured to sample one or more chemical characteristic and/or biological marker. At step 604, a level of the sensed characteristic(s) of the exudate fluid may be measured. The measurement may include processing raw data from sampled data and may be performed by either the MEMS device or reduced pressure deliver system. At step 606, in response to the measured characteristic level, treatment may be caused to be applied or altered to the tissue site. The treatment may include altering reduced pressure treatment, apply a treatment fluid, or a combination thereof. For example, a cleansing treatment fluid, such as a saline solution, may be applied or altered to the tissue site and reduce pressure may be applied to remove the cleansing treatment fluid from the tissue site. Alternative treatment fluids may be applied or altered to the tissue site depending on the characteristic(s) of the exudate fluid.

Although the MEMS device has been described as being incorporated for use in a reduced pressure delivery system that utilizes a conduit for delivering reduced pressure to a tissue site, it should be understood that the MEMS device may be utilized by an integrated reduced pressure delivery system that delivers reduced pressure to the tissue site without utilizing a conduit. Such an integrated reduced pressure delivery system incorporates processing and vacuum pump functionality into a dressing, thereby eliminating a conduit. A MEMS device may communicate with a processing unit either via a wire or wirelessly to assist in delivering medicine or cleansing fluids.

While this description describes MEMS, it should be understood that the principles of the present invention may apply to the use of nano electromechanical systems (NEMS). NEMS devices may be configured to be integrated into a dressing and be in communication with a reduced pressure delivery system, whereby the NEMS device may be wired or wirelessly in communication with a reduced pressure delivery system for use in providing the ability to perform feedback control based on measurements being made at the tissue site.

Although the principles of the present invention have been described in terms of the foregoing embodiments, this description has been provided by way of explanation only, and is not intended to be construed as a limitation of the invention. Those skilled in the art will recognize modifications of the present invention that might accommodate specific patient and tissue treatment environments.

I claim:

1. A reduced pressure delivery system for treating a tissue site of a patient, comprising:
   electromechanical components configured to apply a treatment to the tissue site of the patient;
   a processing unit in communication with said electromechanical components and configured to cause said electromechanical components to activate to apply or alter the treatment to the tissue site;
   at least one conduit configured to deliver the treatment to the tissue site; and
   a micro-electro-mechanical system (MEMS) device including an integration of its components on a common substrate, and configured to sense one or more characteristics of exudate fluid from the tissue site, and further configured to communicate data indicative of the sensed one or more exudate fluid characteristics, said processing unit configured to receive the data from said MEMS device and cause said electromechanical components to apply the treatment to the tissue site of the patient via said at least one conduit.

2. The reduced pressure delivery system according to claim 1, wherein said electromechanical components include at least one valve and at least one pump, the at least one pump configured to apply reduced pressure to the tissue site and the at least one valve configured to enable and disable the reduced pressure to be applied or altered to the tissue site.

3. The reduced pressure delivery system according to claim 2, wherein the at least one pump is further configured to deliver or alter treatment fluid to the tissue site and the at least one valve is configured to enable and disable the treatment fluid to be applied or altered to the tissue site.

4. The reduced pressure delivery system according to claim 1, wherein said MEMS device is wirelessly in communication with said processing unit.

5. The reduced pressure delivery system according to claim 1, wherein said MEMS device is configured to sense a pH level of the exudate fluid.

6. The reduced pressure delivery system according to claim 1, further comprising a dressing in fluid communication with said at least one conduit, and wherein said MEMS device is disposed within said dressing when sensing the one or more characteristics of the exudate fluid of the tissue site.

7. The reduced pressure delivery system according to claim 1, wherein the treatment includes at least one treatment fluid.

8. The reduced pressure delivery system according to claim 1, further comprising an electronic display in communication with said processing unit, said processing unit further configured to generate and display a graphical user interface (GUI) on said electronic display, the GUI including an indicia representative of a characteristic level of the exudate fluid from the tissue site.

9. The reduced pressure delivery system according to claim 1, further comprising an electronic display in communication with said processing unit, said processing unit further configured to generate and display a graphical user interface (GUI) on said electronic display, the GUI including an indicia representative of a characteristic level of the exudate fluid from the tissue site, wherein the one or more characteristics of the exudate fluid include a chemical characteristic, and wherein the indicia representative of a characteristic level of the exudate fluid is representative of a chemical characteristic level.

10. The reduced pressure delivery system according to claim 1, further comprising an electronic display in communication with said processing unit, said processing unit further configured to generate and display a graphical user interface (GUI) on said electronic display, the GUI including an indicia representative of a characteristic level of the exudate fluid from the tissue site, wherein the one or more characteristics of the exudate fluid include a biological marker, and wherein the indicia representative of a characteristic level of the exudate fluid is representative of a biological marker characteristic level.

11. A reduced pressure therapy system for drawing exudate fluid from tissue of a patient and treating the tissue, said reduced pressure therapy system comprising:
   a dressing in fluid communication with the tissue for delivering a vacuum and the treatment fluid to the tissue;
   at least one conduit having one end in fluid communication with said dressing for delivering the vacuum and the treatment fluid thereto;
   an actuating device connected to the other end of said at least one conduit for providing the vacuum thereto in a first state and the treatment fluid thereto in a second state in response to a delivery signal;
   a processing unit in electrical communication with said actuating device to cause the vacuum to be applied or altered during the first state and a delivery signal to be applied or altered to said actuating device during the second state in response to a predetermined therapy for treating the tissue; and
   a MEMS device including an integration of its components on a common substrate, and in fluid communication with the tissue to sense characteristics of the exudate fluid and to generate characteristic data related to the characteristics of the exudate fluid, and in electrical communication with said processing device for transmitting the characteristic data thereto, said processing device applying or altering the delivery signal to said actuating device in response to an analysis of the characteristic data according to the predetermined therapy.

12. The reduced pressure delivery system according to claim 1, wherein said MEMS device is configured to sample multiple characteristics of at least the exudate fluid and environmental conditions at the tissue site.

13. The reduced pressure delivery system according to claim 12, wherein said processing unit is configured to receive data representative of the multiple characteristics of at least the exudate fluid and environmental conditions at the tissue site, and, in response, determining how to apply or alter the delivery signal to said actuating device.

14. The reduced pressure therapy system according to claim 11, wherein said MEMS device is configured to sample multiple characteristics of at least the exudate fluid and environmental conditions at the tissue site.

15. The reduced pressure delivery system according to claim 14, wherein said processing unit is configured to receive data representative of the multiple characteristics of at least the exudate fluid and environmental conditions at the tissue site, and, in response, determining how to apply or alter the delivery signal to said actuating device.

* * * * *